United States Patent [19]

Field et al.

[11] 4,075,250
[45] Feb. 21, 1978

[54] PRODUCTION OF PHENOLS

[75] Inventors: Peter Graham Spencer Field, St. Foy-les-Lyons, France; Ronald Bennett, Chester, England

[73] Assignee: Burmah Oil Trading Limited, Cheshire, England

[21] Appl. No.: 574,755

[22] Filed: May 5, 1975

[30] Foreign Application Priority Data

May 6, 1974 United Kingdom ............. 19826/74

[51] Int. Cl.$^2$ ............................................ C07C 37/08
[52] U.S. Cl. .................................................. 260/621 C
[58] Field of Search ........... 260/621 C, 621 R, 624 C, 260/624 R, 586 P; 252/439

[56] References Cited

U.S. PATENT DOCUMENTS

| | | | |
|---|---|---|---|
| 2,661,375 | 12/1953 | Conner | 260/601 |
| 2,889,368 | 6/1959 | Hiratsuku et al. | 260/593 |
| 3,928,477 | 12/1975 | Fields et al. | 260/621 C |

Primary Examiner—James O. Thomas, Jr.
Assistant Examiner—W. B. Lone
Attorney, Agent, or Firm—Browdy and Neimark

[57] ABSTRACT

Phenols are prepared by decomposing aromatic organic hydroperoxides in the presence of a compound comprising at least one metal atom or cation or at least one non-metallic cation and at least one moiety derivable from an anion of the formula

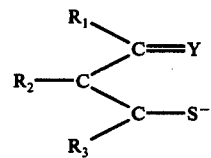

wherein $R_1$, $R_2$ and $R_3$ are each independently a hydrogen atom or a substituted or unsubstituted hydrocarbyl group and Y represents an atom of oxygen or sulphur or a group of the formula

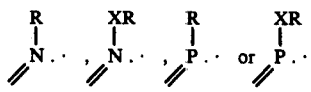

wherein R is a hydrogen atom or a substituted or unsubstituted hydrocarbyl group and X is oxygen or sulphur.

17 Claims, No Drawings

PRODUCTION OF PHENOLS

This invention relates to a process for the production of phenols by decomposing aromatic organic hydroperoxides.

Phenol is commonly produced on a large scale by decomposing cumene hydroperoxide in the presence of an acid catalyst, for example, sulphuric acid or perchloric acid. The mechanism of the reaction, when catalyzed by sulphuric acid is believed to be as follows:

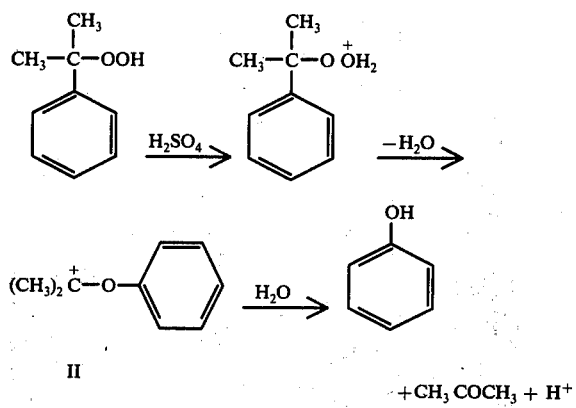

Thus, the cumene hydroperoxide is protonated to form an intermediate I which loses water and rearranges to form the intermediate II which reacts with water to yield phenol and acetone.

The hydroperoxide is normally formed by auto-xidation of cumene (isopropylbenzene) and the latter can be formed by alkylation of benzene with propylene. Other tertiary aralkyl hydroperoxides can be decomposed in the presence of acid catalysts to yield substituted phenols. Thus, for example, para-cresol has been prepared by decomposing para-cymene hydroperoxide.

It has not hitherto been considered commercially practicable to effect the decomposition of hydroperoxides other than tertiary aralkyl hydroperoxides, since firstly the yields of phenols produced have been commercially unattractive and secondly, as in the case of tertiary hydroperoxides, undesirable quantities of high molecular weight by-products are produced when conventional acid catalysts are used.

Furthermore, while the use of conventional acid catalysts to catalyze the decomposition of tertiary aralkyl hydroperoxides to phenols and ketones has led to reported yields of up to about 90 wt % phenol and 80 wt % ketone, based on the hydroperoxide, it is generally found that when using such catalysts, a proportion of the hydroperoxide starting material tends to be converted into very undesirable contaminants by means of competing side reactions. Thus, it is common for the product obtained when cumene hydroperoxide is decomposed in the presence of conventional acid catalysts to contain a proportion of high molecular weight resinous materials and other high boiling materials produced in the reaction. The need to remove these materials can necessitate further process stages and can complicate the recovery of the phenol.

A further disadvantage of the use of conventional acid catalysts is that it is generally necessary to construct the plant used to carry out the decomposition from corrosionresistant materials and this can result in high capital costs. Furthermore, it is generally necessary to remove or neutralize the acid catalyst before the decomposition products are processed to recover phenol.

We have now discovered a novel catalyst for this process the use of which raises the yields of phenols or substituted phenols from secondary aralkyl hydroperoxides to a level which makes this route to the phenols or substituted phenols commercially attractive. Use of this catalyst also may reduce the quantity of high molecular weight by-products formed for both secondary and tertiary hydroperoxides. Also, since the catalyst is not strongly acidic in nature, the vessels used for carrying out the decomposition need not be constructed of such corrosion-resistant materials as are required when conventional acid catalysts are used and there is also no need to remove the catalyst before the phenols are recovered, although this may be effected if desired.

According to the present invention, there is provided a process for producing a phenol or a substituted phenol by decomposing an aromatic organic hydroperoxide, which process comprises effecting the decomposition in the presence of a catalyst comprising a compound, comprising at least one metal atom or cation or at least one non-metallic cation and at least one moiety derivable from an anion of the formula

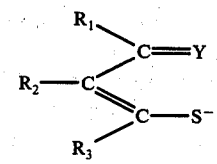

wherein $R_1$, $R_2$ and $R_3$ are each independently a hydrogen atom or a substituted or unsubstituted hydrocarbyl group; and Y represents an atom of oxygen or sulphur or a group of the formula

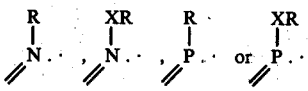

wherein R is a hydrogen or a substituted or unsubstituted hydrocarbyl group and X is oxygen or sulphur and recovering the required phenol or substituted phenol from the decomposition product.

Examples of non-metallic cations include ammonium ions ($NR_4^+$) wherein each R is hydrogen or a group as defined above.

Examples of unsubstituted hydrocarbyl groups R, $R_1$, $R_2$ and $R_3$ are alkyl groups (both straight chained and branched), aryl groups (including alkaryl groups) and aralkyl groups, for example benzyl groups. Preferred alkyl groups are those containing from 1 to 8 carbon atoms, for exmple methyl, ethyl, propyl, isopropyl, n-butyl, iso-butyl, t-butyl, amyl, heptyl and octyl, and most preferably those containing from 1 to 4 carbon atoms.

Preferably, the catalyst comprises a compound of a transition metal, in particular a compound of a transition metal appearing in Group VIII of the Period Table.

Thus, for example, the catalyst may comprise at least one moiety derivable from an anion of the formula (I) defined above and at least one metal atom selected from iron, cobalt and nickel atoms.

The structure of the metal compound used as catalyst in the process of the invention depends, of course, on the identity of the metal and of the group Y and may, for example, be represented as containing the grouping

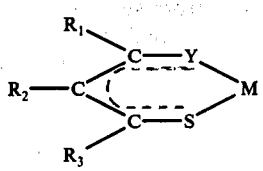

or in complexes of the formulae

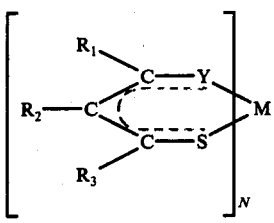

wherein M, Y, $R_1$, $R_2$ and $R_3$ are as defined above and N is the oxidation state of the metal.

Representative examples of compounds which may be used as catalyst in the process of the invention are metal complexes of monothio- and dithio- $\beta$-diketones, which may be represented respectively by the formulae

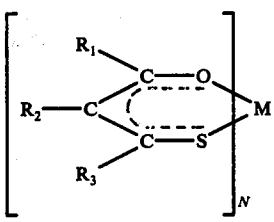

and

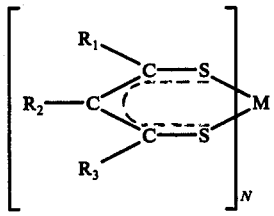

wherein M, N, $R_1$, $R_2$ and $R_3$ are as defined above.

Specific examples of such compounds include the following:

1. Bis (dithio-acetylacetonato) Nickel (II)

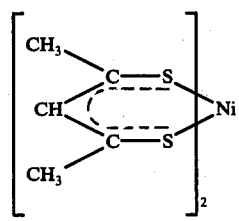

2. Tris(monothio-acetylacetonato) Cobalt (III)

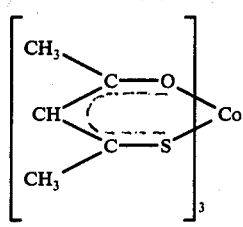

3. Bis(monothio-acetylacetonato) Nickel (II)

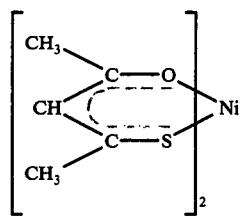

4. Tris (monothio-acetylacetonato) Iron (III)

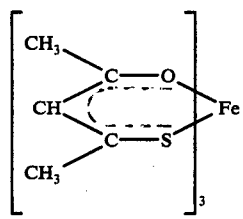

It has been observed surprisingly that by using the process of the invention, increased yields of phenols may be obtained by decomposing secondary aromatic organic hydroperoxides than when conventional acid catalysts are used. Thus, for example, yields in excess of 70 wt % of phenol have been obtained by decomposing ethylbenzene hydroperoxide in accordance with the process of the invention. Furthermore, when aromatic organic hydroperoxides in general are decomposed in accordance with the invention, significantly lower quantities of high molecular weight by-products are formed than when conventional acid catalyst are used.

The aromatic organic hydroperoxide starting material employed in the process of the present invention may be an aryl mono-alkyl hydroperoxide, which preferably contains from 2 to 24, more preferably 2 to 16 and especially 2 to 12, carbon atoms in the alkyl moiety. An example of such a hydroperoxide is ethyl benzene hydroperoxide. Alternatively, a substituted -aryl alkyl hydroperoxide may be used, i.e. a hydroperoxide in which the aryl group bears one or more substituents e.g. selected from halogen atoms and alkyl, alkoxy and nitro groups. Decomposition of such hydroperoxides produces a correspondingly substituted phenol. In yet another alternative a dialkylaryl dihydroperoxide may be used, i.e. a compound having an aryl nucleus substituted by two secondary alkylhydroperoxide groups, in which case a dihydric phenol will result from the decomposition. Such hydroperoxides may likewise bear one or more substituents thus enabling correspondingly substituted dihydric phenols to be obtained.

The decomposition of the hydroperoxide in the presence of the catalyst proceeds very readily and may be carried out under a wide variety of reaction conditions. Preferably the reaction temperature is not permitted to reach too high a level since this could lead to the thermally initiated decomposition of the hydroperoxide, producing undesirable by-products, and in an extreme case might lead to decomposition becoming too rapid and uncontrollable, and potentially explosive. A reaction temperature of from ambient to 180° C is preferred, more preferably ambient to 150° C and especially 100° C to 140° C. The decomposition of the hydroperoxide may be sufficiently exothermic to make it desirable to control the reaction temperature in order to maintain it at the desired level. Conventional techniques can be used for this purpose, such as external cooling and/or regulating the rate at which the hydroperoxide is brought into contact with the catalyst.

Preferably the aldehyde co-product of the decomposition is continuously removed during the decomposition reaction in order to reduce the possibility of unwanted side reactions between the aldehyde and other components of the decomposition product. Thus, for example, the aldehyde may be distilled off and collected in a condenser. Removal of the aldehyde may be assisted by conducting the decomposition under reduced pressure, but generally the pressure at which the decomposition is carried out is not narrowly critical and conveniently atmospheric pressure may be used, particularly in the case where the co-product aldehyde is sufficiently volatile at the reaction temperature to be distilled off at atmospheric pressure.

The time required for completion of the reaction will depend, inter alia, on the reaction temperature but even at very low reaction temperatures is normally not more than 3 or 4 hours. At preferred reaction temperatures the decomposition will in most cases be completed within, e.g. 5 to 50 minutes at 150° C or within 1½ to 2 hours, usually not more than 1 hour, at 80° C to 120° C.

In order to moderate the decomposition, the process of the present invention is generally carried out in the presence of an inert solvent, i.e. a solvent which does not react with the hydroperoxide or its decomposition products. Thus in the case of a hydroperoxide which is solid at the reaction temperature it is preferred to dissolve the hydroperoxide in an inert solvent. The inert solvent can also be used if desired even when the hydroperoxide is liquid at the reaction temperature used. If used the inert solvent is preferably present in an amount such as to provide a solution containing from 1% to 50%, more preferably 5% to 25%, by weight of the hydroperoxide. Examples of inert solvents include benzene, toluene, xylene, ethylbenzene, chlorobenzene and nitrobenzene.

Very small quantities of the catalyst may be successfully employed in the process of the present invention. Larger quantities can also be used. However, this is unnecessary and wasteful and in some cases larger quantities of catalyst may be detrimental. In a preferred embodiment of the invention the ratio of catalyst to hydroperoxide is from 1:10,000 to 1:1000, preferably 1:5,000 to 1:1,000.

The hydroperoxides used in the process of the present invention may be prepared by the usual methods, such as autoxidation of the alkyl aryl compound. The alkyl aryl starting materials for the autoxidation may also be prepared by the usual methods such as alkylation of aryl compounds with an olefin.

The phenol and the aldehyde produced in accordance with the process of the invention may be recovered by conventional methods, for example by fractional distillation and in general the purification techniques used in the conventional acid-catalyzed process may be employed, although of course the process steps concerned with the removal of the catlyst may be omitted.

The invention will now be illustrated by the following Examples:

EXAMPLE 1

0.0022 parts by weight of bis (dithio acetonato)nickel (II), 25 parts by weight of ethylbenzene and 3 parts by weight of ethylbenzene hydroperoxide were weighed into a glass pressure vessel and heated on an oil bath maintained at 120° C. (mole ratio of ethylbenzene hydroperoxide to catalyst = 3011:1).

The temperature of the reaction mixture was maintained at 120° C for 30 minutes whilst agitating the reactor contents using a magnetic stirrer.

The reaction mixture was then cooled and analyzed for residual hydroperoxide and phenol.

The following analysis was obtained:

Residual Hydroperoxide: 0.03 parts by weight
Phenol produced: 1.56 parts by weight
Percentage conversion: 99.0%
Selectivity to phenol: 80.4%

EXAMPLES 2 to 4

The procedure of Example 1 was repeated using various catalysts and the results are shown in the following Table:

TABLE

| Ex. | Catalyst | Parts by weight of Catalyst | Ethylbenzene Hydroperoxide to Catalyst Ratio | Mass of residual Hydroperoxide (g) | Mass of Phenol Produced (parts by weight) | Percentage Conversion | Percentage Selectivity to Phenol |
|---|---|---|---|---|---|---|---|
| 2 | Tris(monothio-acetylacetonato) Cobalt (III) | 2.8 | 3011:1 | 0.04 | 1.51 | 98.6 | 78.1 |
| 3 | Bis(monothio-acetylacetonato) Nickel (II) | 2.8 | 3011:1 | 1.61 | 0.40 | 42.7 | 47.8 |
| 4 | Tris(monothio-acetylacetonato) Iron (III) | 2.8 | 2990:1 | 0.03 | 1.52 | 99.0 | 78.7 |

We claim:
1. In the process comprising decomposing an aralkyl hydroperoxide, in which the aryl nucleus is substituted by at least one alkylhydroperoxide group containing from 2 to 24 carbon atoms and said aryl nucleus may be further substituted by one or more other substituents selected from halogen atoms and alkyl, alkoxy and nitro groups, to produce a correspondingly substituted or unsubstituted mono- or polyhydric phenol, the improvement comprising:
effecting the decomposition at a temperature of from ambient temperature to 180° C in the presence of a catalyst comprising a compound of the formula

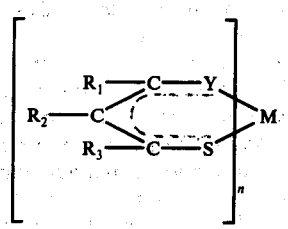

wherein $R_1$, $R_2$ and $R_3$ are each independently selected from the group consisting of hydrogen atoms, straight chained and branched alkyl groups, phenyl, alkylphenyl groups and phenylalkyl groups, wherein the alkyl moieties contain from 1–8 carbon atoms, Y is an atom of oxygen or sulphur, M is a metal atom selected from the transition metals in Group VIII of the Periodic Table, and n is the oxidation state of the metal, said oxidation state being 2 or 3; and recovering the produced phenol or substituted phenol from the decomposition product.

2. A process according to claim 1 in which $R_1$, $R_2$ and $R_3$ are selected from alkyl groups containing from 1 to 8 carbon atoms and hydrogen atoms.

3. A process according to claim 2 in which $R_2$ is a hydrogen atom.

4. A process according to claim 3 in which $R_1$ and $R_3$ are methyl groups.

5. A process according to claim 1 in which the catalyst comprises bis(dithio-acetylacetonato)Nickel (II).

6. A process according to claim 1 in which the catalyst comprises tris(monothio-acetylacetonato)Cobalt-(III).

7. A process according to claim 1 in which the catalyst comprises bis(monothio-acetylacetonato)Nickel-(II).

8. A process according to claim 1 in which the catalyst comprises bis(monothio-acetylacetonato(Iron)III).

9. A process according to claim 1 in which said aralkyl hydroperoxide is secondary hydroperoxide.

10. A process according to claim 1 in which said aralkyl hydroperoxide is an aryl mono-alkyl hydroperoxide containing 2 to 24 carbon atoms in the alkyl moiety.

11. A process according to claim 10 in which the mono-alkyl hydroperoxide contains from 2 to 12 carbon atoms in the alkyl moiety.

12. A process according to claim 11 in which said aralkyl hydroperoxide is ethylbenzene hydroperoxide.

13. A process according to claim 1 in which the decomposition is carried out in the presence of an inert solvent.

14. A process according to claim 1 in which the ratio of catalyst to hydroperoxide is from 1:10,000 to 1:1,000.

15. A process according to claim 9 in which the ratio of catalyst to hydroperoxide is from 1:5,000 to 1:1,000.

16. A process in accordance with claim 1 wherein M is iron, nickel or cobalt.

17. A process in accordance with claim 2 wherein M is iron, nickel or cobalt.

* * * * *